United States Patent [19]

Pawlowski et al.

[11] Patent Number: 5,286,602
[45] Date of Patent: Feb. 15, 1994

[54] ACID-CLEAVABLE COMPOUNDS, POSITIVE-WORKING RADIATION-SENSITIVE MIXTURE CONTAINING THESE COMPOUNDS, AND RADIATION-SENSITIVE RECORDING MATERIAL PRODUCED WITH THIS MIXTURE

[75] Inventors: Georg Pawlowski, Wiesbaden; Horst Roeschert, Ober-Hilbersheim; Walter Spiess, Dieburg, all of Fed. Rep. of Germany; Ralph Dammel, Coventry, R.I.

[73] Assignee: Hoechst Aktiengesellschaft, Frankfurt am Main, Fed. Rep. of Germany

[21] Appl. No.: 871,009

[22] Filed: Apr. 20, 1992

[30] Foreign Application Priority Data

Apr. 20, 1991 [DE] Fed. Rep. of Germany ....... 4112968

[51] Int. Cl.$^5$ ............................................. C08G 12/12
[52] U.S. Cl. .................................. 430/270; 528/264;
528/266; 430/326; 430/905; 560/165; 560/166;
564/60; 564/153
[58] Field of Search ............... 528/264, 266; 430/270,
430/326, 905; 560/165, 166; 564/60, 153

[56] References Cited

U.S. PATENT DOCUMENTS

| | | | |
|---|---|---|---|
| 3,515,552 | 6/1970 | Smith | 96/35.1 |
| 4,101,323 | 7/1978 | Buhr et al. | 96/35 |
| 4,247,611 | 1/1981 | Sander et al. | 430/286 |
| 4,696,888 | 9/1987 | Buhr | 430/270 |
| 5,037,721 | 8/1991 | Doessel | 430/177 |

FOREIGN PATENT DOCUMENTS

| | | |
|---|---|---|
| 0232972 | 8/1987 | European Pat. Off. |
| 1163324 | 9/1969 | United Kingdom |
| 1381471 | 1/1975 | United Kingdom |

OTHER PUBLICATIONS

Crivello, "Possibilities for Photoimaging Using Onium Salts", Polymer Engineering and Science, Mid-December, 1983, vol. 23, pp. 953-955.

Houlihan et al., "An Evaluation of Nitrobenzyl Ester Chemistry for Chemical Amplification Resists" SPIE, Advances in Resist Technology and Processing, 1988, vol. 920, pp 67-73.

Willson, "Organic Resist Materials-Theory and Chemistry", Introduction to Microlithography, 1983, pp. 88-159.

Primary Examiner—John Kight, III
Assistant Examiner—Rachel Johnson
Attorney, Agent, or Firm—Foley & Lardner

[57] ABSTRACT

Compounds having repeating units of the formula I

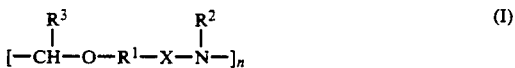

in which $R^1$ is an alkylene, cycloalkylene, alkenylene, alkynylene, or arylenebisalkyl group, in which one or more aliphatic $CH_2$ groups may be replaced by oxygen or sulfur atoms, $R^2$ is an alkyl, alkenyl, alkynyl, cycloalkyl, alkoxyalkyl, aryl, aralkyl or aryloxyalkyl radical, $R^3$ is an alkyl or aryl radical, X is —CO—, —O—CO— or —NH—CO—, and n is an integer greater than 1, especially from 3 to 50.

are cleavable by acid and, in combination with photolytic acid donors and alkali-soluble binders, are constituents of positive-working mixtures which are used especially in recording materials for UV radiation and high-energy radiation. The materials are distinguished by a high resolution in conjunction with high image contrast.

20 Claims, No Drawings

ACID-CLEAVABLE COMPOUNDS, POSITIVE-WORKING RADIATION-SENSITIVE MIXTURE CONTAINING THESE COMPOUNDS, AND RADIATION-SENSITIVE RECORDING MATERIAL PRODUCED WITH THIS MIXTURE

BACKGROUND OF THE INVENTION

Field of the Invention

The invention relates to novel acid-cleavable N,O-acetals and to a radiation-sensitive mixture which is positive-working, i.e., which becomes soluble as a result of irradiation, which contains these compounds. The mixture contains (a) a binder which is insoluble in water and soluble or at least swellable in aqueous alkaline solutions,
(b) a compound which generates a strong acid under the action of actinic radiation, and
(c) a compound which has at least one acid-cleavable C—O—C bond and is convertible by cleavage into products having an enhanced solubility in aqueous alkaline solutions.

The invention also relates to a radiation-sensitive recording material which is produced with this mixture and which is suitable for producing photoresists, electronic components, printing plates or for chemical milling.

Description of Related Art

To produce microelectronic circuits, several lithographic techniques are currently being used. Using g-line lithography (436 nm), which is usually applied to conventional diazonaphtho-quinone/novolak formulations, resist images with a resolution of down to 0.8 μm can be produced. Images of even finer structures (down to 0.5 μm) on a resist layer can be obtained by means of i-line lithography (365 nm). More recent modifications of i-line lithography, such as, for example, phase-shifting mask technology, allow a further reduction in the size of the structures, of which images are to be formed, down to about 0.35 μm or less. An even higher resolution can be achieved with UV2 photoresists. In this case, two irradiation techniques are used: UV2 wide band exposure (240 to 260 nm) or exposure with KrF-excimer lasers which emit at 248 nm.

The continuing reduction in the size of the structures, for example in chip manufacture down into the range of less than 1 μm, requires modified lithographic techniques. To form images of such fine structures, radiation of a short wavelength is used, such as high-energy UV light, electron beams and X-rays. The radiation-sensitive mixture must be adapted to the shortwave radiation. A compilation of the requirements to be met by the radiation-sensitive mixture is given in the article by C. G. Willson "Organic Resist Materials—Theory and Chemistry" [Introduction to Microlithography, Theory, Materials, and Processing, editors L. F. Thompson, C. G. Willson, M. J. Bowden, ACS Symp. Ser., 219, 87 (1983), American Chemical Society, Washington].

There is therefore an increased demand for radiation-sensitive mixtures which can be used in the more recent technologies, such as mid-UV or deep-UV lithography [exposure, for example, with excimer lasers at wavelengths of 305 nm (XeF), 248 nm (KrF), 193 nm (ArF)], electron beam lithography or X-ray lithography, and which, furthermore, are preferably sensitive in a wide spectral range and correspondingly can also be used in conventional UV lithography.

Positive-working radiation-sensitive mixtures for producing radiation-sensitive recording materials are known. Mixtures which contain o-quinone-diazide derivatives in binders soluble in aqueous alkaline media, for example novolaks or polyhydroxystyrenes, are commercially available. However, the sensitivity of these materials to actinic radiation, and especially high-energy short-wave radiation, such as light from a KrF-excimer laser having a wavelength of 248 nm or electron beams, is inadequate.

Positive-working radiation-sensitive mixtures are also known in which an acid is generated by the action of actinic radiation on a photoinitiator contained in this mixture. This acid then, in a subsequent reaction, renders an acid-cleavable compound likewise contained in the mixture, soluble in the irradiated areas under the action of an appropriate, preferably aqueous alkaline, developer. Such materials are in general distinguished by an enhanced sensitivity to actinic radiation.

Numerous mixtures of acid-cleavable, solubility-inhibiting compounds are known which always contain a small quantity of a photolytic acid generator whose acidic photolysis product initiates the cleavage. These mixtures, some of which have high sensitivities to actinic radiation, are designated as chemically amplified, photocatalytic 3-component systems since they contain, as essential constituents, a polymeric binder soluble in aqueous alkaline solutions, in most cases a novolak resin, a photoactive compound and a solubility inhibitor.

Amongst these mixtures, those which contain either monomeric or oligomeric acetal units as the acid-cleavable components have gained a certain commercial importance. These mixtures have, however, certain disadvantages since they possess only a limited stability on the substrate materials to which they have to be applied, and lead to unsatisfactory, non-reproducible images of the original. This can be improved by introducing additional protective layers, for example according to DE-A 3,621,376 which is equivalent to U.S. Pat. No. 4,840,867. Furthermore, it is observed generally that the process window, i.e., the processing latitude, for the exposure of these mixtures is very narrow and frequently not unambiguously reproducible, which manifests itself in unsatisfactory reproductions of originals. In particular, the quality of the image reproduction greatly depends on the time difference between exposure and development, the so-called delay time. The reasons for the deterioration in image reproduction are not known in detail and have not been adequately investigated. In principle, it must be assumed that diffusion processes which cause this behavior are not easily controllable. In addition, however, it may be presumed that, during drying of the mixture on a substrate material, partial vaporization of the photoinitiator or of the acid-unstable compound, or segregation of the individual mixture constituents takes place, which is observed with particular frequency in the case of acid-unstable compounds having a low solubility in the usual coating solvents.

The decisive disadvantage of the known compounds containing acetal groups is, however, the fact that the solubility differentiation, resulting from their cleavage between exposed and unexposed image areas, is in general inadequate. The cause of this is probably that either the acetal derivative used as a solution inhibitor has an insufficient inhibiting property and, in imagewise differentiation, in addition to the exposed image areas those areas are also severely attacked and removed which were not exposed, or that the exposed areas do not have a solubility sufficient to permit an imagewise differentiation during development. The problem can be summarized by saying that it is not possible to provide a material which causes a sufficiently large solubility difference between exposed and unexposed areas using the known compounds. Whereas this effect is in general still acceptable in the case of the novolak resins used according to the state of the art, it is observed when other polymers are used that the known acetal derivatives virtually no longer show any inhibiting action and thus no longer permit an image differentiation as required in practice.

There is therefore a demand for radiation-sensitive mixtures which do not show the disadvantages described above, possess a reactivity suitable in practice and, in particular, permit good imagewise differentiation in combination with the most diverse matrix polymers.

SUMMARY OF THE INVENTION

It is an object of the invention to propose novel acid-cleavable compounds and a radiation-sensitive mixture which contains these compounds. The novel acid-cleavable compounds should have a sufficient reactivity on the one hand and a stability meeting the needs of practice on the other. Furthermore, they should form homogeneous mixtures with the most diverse matrix polymers and, in the unirradiated form, should act as an efficient solution inhibitor, while their cleavage products should assist the developability of the exposed areas in aqueous alkaline developers. The mixture containing the acid-cleavable compounds should also be as stable as possible both in solution and on the substrates used in practice, and allow a differentiation between exposed and unexposed areas, which permits the highest possible resolutions with virtually perpendicular flanks.

Furthermore, it is an object of the invention to provide a radiation-sensitive mixture which largely avoids segregation of the compound (b) and the solubility-differentiating compound (c) and thus likewise allows an enhanced differentiation between image areas and non-image areas.

It is a further object of the present invention to provide a recording material which provides a defect-free image of the mask and has high flank stability, and which is suitable for use in the production of photoresists, electronic components, and printed plates It is also an object of the present invention to provide a process for producing such a recording material.

It is a further object of the invention to provide a process for preparing an image pattern using the recording material.

In accomplishing the foregoing objectives, there has been provided, in accordance with one aspect of the present invention, a compound which has at least one acid-cleavable C—O—C bond and whose acid cleavage products are more readily soluble in aqueous alkaline solutions than the compound itself, having repeating units of the formula I

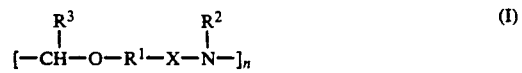

in which

R$^1$ is an alkylene, cycloalkylene, alkenylene, alkynylene, or arylenebisalkyl group, in which one or more aliphatic CH$_2$ groups may optionally be replaced by oxygen or sulfur atoms, R$^2$ is an alkyl, alkenyl, alkynyl, cycloalkyl, alkoxyalkyl, aryl, aralkyl or aryloxyalkyl radical, R$^3$ is an alkyl or aryl radical, X is one of the groups —CO—, —O—CO— or —NH—CO—, n is an integer greater than 1 and R$^1$, R$^2$, R$^3$ and X may have the same or different meanings in different units.

There has further been provided a positive-working radiation-sensitive mixture comprising this compound, at least one binder which is insoluble in water and soluble or at least swellable in aqueous alkaline solutions, and at least one compound which generates a strong acid under the action of actinic radiation.

There has further been provided a positive-working radiation-sensitive recording material comprising a support and a radiation-sensitive layer, wherein the layer comprises a radiation-curable mixture as described above.

There has also been provided a method of producing such a recording material which comprises dissolving the radiation sensitive mixture in a solvent, applying the resulting solution to the support, and removing the solvent.

There has further been provided a method of preparing an image pattern comprising irradiating the radiation-sensitive layer imagewise, optionally heating the irradiated layer, treating the layer with a developer which removes the irradiated areas of the layer, and optionally post-hardening the developed layer structures.

Further objects, features, and advantages of the present invention will become apparent from the detailed description of preferred embodiments that follows.

DETAILED DESCRIPTION OF THE PREFERRED EMBODIMENTS

Preferred are compounds of the formula I, which have a certain viscosity, i.e. which have a K-value in the range of from 7 to 19 (measured in a 20% (w/w) propylene glycol methyl ether acetate solution; K-values as defined by H. Fickentscher, Cellulosechemie 13 [1932]60). The molecular weight M$_w$, based on a polystyrene standard, of these compounds is in the range of from 300 to 8,000, n is thus preferably an integer from 2 to 50, especially from 3 to 20.

Those compounds of the formula I are preferred in which

R$^1$ is an alkylene, alkenylene or alkynylene group having 2 to 18 carbon atoms, in which 1 to 3 CH$_2$ groups are optionally replaced by oxygen and/or sulfur atoms, a cycloalkylene group having 4 to 18 carbon atoms, an aralkylene group having 7 to 18 carbon atoms or an arylenebisalkyl group having 8 to 18 carbon atoms, R$^2$ is an alkyl radical having 1 to 12 carbon atoms, an alkenyl or alkynyl radical having 2 to 12 carbon atoms, an alkoxyalkyl radical having 3 to 12 carbon atoms, a cycloalkyl radical having 4 to 12 carbon atoms, an aryl radical having 6 to 12 carbon atoms, an aralkyl radical having 7 to 12 carbon atoms or an aryloxyalkyl radical having 8 to 12 carbon atoms, and n is an integer greater than 3.

Those compounds of the formula I are particularly preferred in which $R^1$ is an unbranched or branched alkylene, cycloalkylene, cycloalkylenedialkyl, alkenylene or alkynylene group each having up to 8 carbon atoms, wherein a carbon is optionally replaced by an oxygen or sulfur atom, or an arylenedialkyl group having 8 to 12 carbon atoms, $R^2$ is an alkyl, alkenyl, alkynyl, cycloalkyl or alkoxyalkyl radical having up to 6 carbon atoms or an aryl, arylalkyl or aryloxyalkyl radical having 7 to 12 carbon atoms, $R^3$ is an alkyl radical having 1 to 6 carbon atoms, an unsubstituted or substituted mononuclear or polynuclear aryl radical having 6 to 12 carbon atoms, and n is an integer between 3 and 50.

Those compounds of the formula I are very particularly preferred in which $R^1$ is an unbranched or branched alkylene group having 2 to 4 carbon atoms, $R^2$ is an alkyl, alkenyl, alkynyl or cycloalkyl radical having up to 6 carbon atoms and $R^3$ is an alkyl radical having 1 to 6 carbon atoms or an unsubstituted or substituted six-membered aryl radical.

According to the present invention, $R^3$ can, for example, be selected from the following: methyl, ethyl, n-propyl, isopropyl, n-butyl, isobutyl, n-hexyl, phenyl, 4-acetylaminophenyl, 4-acetoxyphenyl, 3- and 4-benzyloxyphenyl, 3-benzyloxy-4- and 4-benzyloxy-3-methoxyphenyl, biphenyl-4-yl, 3,5-bis-trifluoromethylphenyl, 2-, 3- and 4-fluorophenyl, 2-, 3- and 4-chlorophenyl, 2-, 3- and 4-bromophenyl, 4-iodophenyl, 2-, 3- and 4-cyanophenyl, 3-and 4-methyl-, -ethyl-, -propyl-, -isopropyl-, -butyl-, -isobutyl-, -t-butyl-, -pentyl-, -hexyl-, -cyclohexyl-, -nonyl- and -dodecyl-phenyl, 2-, 3- and 4-methoxy-, -ethoxy-, -isopropoxy-,-butoxy-, -pentyloxy-, -octyloxy-and -decyloxyphenyl, 2,3-, 2,4-, 2,6-, 3,4- and 3,5-difluoro-, -dichloro- and -dibromophenyl, 3-(3,4-dichlorophenoxy)-phenyl, 3-(3,5-dichlorophenoxy)-phenyl, 3-bromo-4-fluorophenyl, 5-bromo-2,4-dimethoxyphenyl, 2-chloro-6-fluorophenyl, 2-chloro-5-, 2-chloro-6-, 4-chloro-3- and 5-chloro-2-nitrophenyl, 3-(4-chlorophenoxy)-phenyl, 3,4-bis-benzyloxyphenyl, 2,3-, 2,4-, 2,5-, 3,4- and 3,5-dimethoxy-, -diethoxy-, -dibutoxy- and -dihexyloxyphenyl, 2,4-dimethoxy-3-methylphenyl, 2-ethoxy-5-methoxyphenyl, 3-chloro-4-methylphenyl, 2,4- and 2,5-dimethylphenyl, 2-(2-methoxyethyl)-, 2-(2-ethoxyethyl)-and2-(2-butoxyethyl)-phenyl, 3-(2-methoxyethyl)-, 3-(2-ethoxyethyl)- and 3-(2-butoxyethyl)-phenyl, 4-(2-methoxyethyl)-, 4-(2-ethoxyethyl)-and 4-(2-butoxyethyl)-phenyl, 2,6-dinitrophenyl, 2,4,6-trimethylphenyl, 3,4,5-trimethoxy-and -triethoxy-phenyl, 2,3- and 3,4-methylenedioxyphenyl, 2- and 3-thienyl, 2-fluorenyl, 9-anthryl, 5-bromo-2-thienyl, 3-methyl-2-thienyl, 5-methyl-2-thienyl, 5-nitrofuryl, 10-chloro-9-anthryl and ferrocenyl.

These radicals are preferred particularly for the reason that the starting compounds on which they are based are commercially available. Compounds can also be selected so that the absorption of the prepared N,O-acetal according to the invention in the wavelength range of the radiation used is kept as low as possible. Further starting compounds are accessible in a simple manner.

The preparation of the compounds according to the invention of the formula I can be carried out by methods known per se via a multi-stage synthesis. This requires the provision of suitable alcohols which contain amide, urethane or urea groups and whose preparation is described below. These are reacted in a subsequent step with suitable monomeric acetals or acetal precursors, for example, according to EP-A 0, 312, 751. The terminal groups of the compounds of formula I are thus usually HO—$CHR^3$—O—$R^1$—X—$NR^2$— and —CH-$R^3$—O—$R^1$—X—$NHR^2$. The synthesis is illustrated below by reference to some examples according to the invention. P.b.w. means parts by weight.

PREPARATION EXAMPLE 1

1st stage: 59.1 p.b.w. of n-propylamine were added to 88.1 p.b.w. of ethylene carbonate. The mixture was stirred for 5 hours at 70° C. and distilled in vacuo. A colorless oil distilled over at 102 to 105° C./0.06 mm Hg (2-hydroxyethyl N-propyl-carbamate).

2nd stage: 15.2 p.b.w. of benzaldehyde dimethylacetal, prepared by acetalization of benzaldehyde and methanol, were heated under reflux with 29.4 p.b.w. of the urethane-alcohol described in 200 p.b.w. of toluene in the presence of 0.2 p.b.w. of p-toluenesulfonic acid. From time to time, the toluene/methanol mixture formed was distilled off until, after about 6 hours, the top temperature remained constant at 110° C. for a prolonged period. The mixture was cooled down and washed with a dilute sodium hydroxide solution and then with water until neutral. After drying, the toluene was distilled off in a rotary evaporator and the remaining residue was condensed in a high vacuum (0.01 mm Hg) at 200° C. This gave an oligomeric compound ($M_w \approx 2,000$; $K \approx 12.6$) of the formula I in which $R^1$ is an ethylene group, X is the group —O—CO—, $R^2$ is an n-propyl group and $R^3$ is a phenyl group (Compound 1 below).

PREPARATION EXAMPLE 2

Compound 1 was also obtained by the following route: 15.2 p.b.w. of benzaldehyde dimethylacetal were mixed with 14.7 p.b.w. of the urethane-alcohol described above and, after addition of 0.2 p.b.w. of p-toluenesulfonic acid, slowly heated to 160° C. The methanol formed was distilled off. After about 2 hours, a vacuum (0.01 mm Hg) was applied, and the mixture was heated to 200° C. The mixture was exposed to these conditions for a further 2 hours. A highly viscous oil remained whose properties were virtually identical to those of Compound 1.

PREPARATION EXAMPLE 3

Compound 1 was also obtainable by the following route:

15.2 p.b.w. of benzaldehyde dimethylacetal, prepared by acetalization of benzaldehyde with methanol, were heated under reflux with 29.4 p.b.w. of the urethane-alcohol described in Example 1 in 200 p.b.w. of toluene in the presence of 0.2 p.b.w. of p-toluenesulfonic acid. From time to time, the toluene/methanol mixture formed was distilled off until, after about 6 hours, the top temperature remained constant at 110° C. for a prolonged period. The mixture was cooled down and washed with a dilute sodium hydroxide solution and then with water until neutral. After concentrating the solvent, an oily residue remained which was re-precipitated from hot diisopropyl ether. On cooling, white crystals having a melting point of 54.5° C. crystallized out of the solution. 19.1 p.b.w. of these crystals were slowly heated to 160° C. with stirring with 7.6 p.b.w. of benzaldehyde dimethylacetal and 0.2 p.b.w. of p-toluenesulfonic acid. The methanol formed was distilled off. After about 2 hours, a vacuum (0.01 mm Hg) was applied, and the mixture was heated to 200° C. The mixture was exposed to these conditions for a further 2 hours. A highly viscous oil remained whose properties were virtually identical to those of Compound 1.

PREPARATION EXAMPLE 4

1st stage: 101.2 p.b.w. of n-hexylamine were added to 88.1 p.b.w. of ethylene carbonate. The mixture warmed up and was stirred for 5 hours at 70° C. and distilled in vacuo. A colorless oil which distilled over at 117 to 119° C./0.05 mm Hg (2-hydroxyethyl N-hexyl-carbamate).

2nd stage: 19.6 p.b.w. of piperonal dimethylacetal were heated under reflux with 38.0 p.b.w. of the urethane-alcohol described above in 200 p.b.w. of toluene in the presence of 0.2 p.b.w. of p-toluenesulfonic acid. From time to time, the toluene/methanol mixture formed was distilled off until, after about 6 hours, the top temperature remained constant at 110° C. for a prolonged period. The mixture was cooled down and washed with a dilute sodium hydroxide solution and then with water until neutral. After drying, the toluene was distilled off in a rotary evaporator and the remaining residue was condensed in a high vacuum (0.01 mm Hg) at 200° C. This gave an oligomeric compound of the formula I in which $R^1$ is an ethylene group, X is the group —O—CO—, $R^2$ is the n-hexyl group and $R^3$ is the 4-piperonyl group (Compound 2 below).

PREPARATION EXAMPLE 5

1st stage: 73.1 p.b.w. of i-butylamine were added to 88.06 p.b.w. of ethylene carbonate. The mixture warming up was stirred for 5 hours at 70° C. and distilled in vacuo. A colorless oil distilled over at 101 to 104° C./0.06 mm Hg (2-hydroxyethyl N-isobutyl-carbamate).

2nd stage: 18.6 p.b.w. of 4-chlorobenzaldehyde dimethylacetal were heated under reflux with 32.2 p.b.w. of the urethane-alcohol described above in 200 p.b.w. of toluene in the presence of 0.2 p.b.w. of p-toluenesulfonic acid. The toluene/methanol mixture formed was distilled off at intervals until, after about 6 hours, the top temperature remained constant at 110° C. over a prolonged period. The mixture was cooled down and washed with a dilute sodium hydroxide solution and then with water until neutral. After drying, the toluene was evaporated off and the remaining residue was condensed in a high vacuum (0.01 mm Hg) at 200° C. This gave an oligomeric compound of the formula I in which $R^1$ is an ethylene group, X is the group —O—CO—, $R^2$ is an i-butyl group and $R^3$ is a 4-chlorophenyl group (Compound 3).

PREPARATION EXAMPLE 6

1st stage: 21.3 p.b.w. of propyl isocyanate and 25 p.b.w. of diethyl ether were added dropwise at room temperature to 20.6 p.b.w. of aminopropanol in 250 p.b.w. of diethyl ether and 25 p.b.w. of isopropanol. The product which had precipitated was filtered off with suction (N-(3-Hydroxypropyl)-N'-propyl-urea, white powder, melting point 76° C.).

2nd stage: 15.2 p.b.w. of benzaldehyde dimethylacetal were heated under reflux with 32.2 p.b.w. of the urea-alcohol described above in 200 p.b.w. of toluene in the presence of 0.2 p.b.w. of p-toluenesulfonic acid. From time to time, the toluene/methanol mixture formed was distilled off until, after about 6 hours, the top temperature remained constant at 110° C. for a prolonged period. The mixture was cooled down and washed with a dilute sodium hydroxide solution and with water until neutral. After drying, the toluene was evaporated off and the remaining residue was condensed in a high vacuum (0.01 mm Hg) at 220° C. This gave an oligomeric compound of the formula I in which $R^1$ is a propylene group, X is the group —NH—CO—, $R^2$ is an n-propyl group and $R^3$ is a phenyl group (Compound 4 below).

PREPARATION EXAMPLE 7

1st stage: 139.1 p.b.w. of butyl isocyanate were added dropwise to a mixture of 200 p.b.w. of ethylene glycol and 0.5 p.b.w. of diazabicyclo[2,2,2]octane in 200 p.b.w. of tetrahydrofuran. The mixture warmed up, and was stirred for 5 hours at 70° C. and distilled in vacuo. A colorless oil distilled over at 110° to 112° C./0.03 mm Hg (2-hydroxyethyl N-butyl-carbamate).

2nd stage: 19.6 p b w of piperonal dimethylacetal were heated under reflux with 32.2 p.b.w. of the urethane-alcohol described above in 200 p.b.w. of toluene in the presence of 0.2 p.b.w. of p-toluenesulfonic acid. The toluene/methanol mixture formed was distilled off at intervals until, after about 6 hours, the top temperature remained constant at 110° C. for a prolonged period. The mixture was cooled down and washed with dilute sodium hydroxide solution and then with water until neutral. After drying, the toluene was distilled off and the remaining residue was condensed in a high vacuum (0.01 mm Hg) at 200° C. This gave an oligomeric compound of the formula I in which $R^1$ is an ethylene group, X is the group —O—CO—, $R^2$ is an n-butyl group and $R^3$ is a [1,3]benzodioxol-5-yl group (Compound 5 below).

PREPARATION EXAMPLE 8

1st stage: 73.1 p.b.w. of isobutylamine were added to 88.06 p.b.w. of ethylene carbonate. The mixture warmed up, and was stirred for 5 hours at 70° C. and distilled in vacuum. Colorless oil which distils over at 101° to 104° C./0.06 mm Hg.

2nd stage: 25.8 p.b.w. of 4-benzyloxy-benzaldehyde dimethylacetal were heated under reflux with 32.2 p.b.w. of the urethane-alcohol described above in 200 p.b.w. of toluene in the presence of 0.2 p.b.w. of p-toluenesulfonic acid. The toluene/methanol mixture formed was distilled off at intervals until, after about 6 hours, the top temperature remained constant at 110° C. for a prolonged period. The mixture was cooled down and washed with a dilute sodium hydroxide solution and then with water until neutral. After drying, the toluene was evaporated off and the remaining residue was condensed in a high vacuum (0.01 mm Hg) at 200° C. This gave an oligomeric compound of the formula I in which $R^1$ is an ethylene group, X is the group —O—CO—, $R^2$ is a butyl group and $R^3$ is a 4-benzyloxyphenyl group (Compound 6 below).

Further compounds were prepared in a corresponding manner by known methods; a listing of particularly preferred compounds for the preparation of radiation-sensitive mixtures is given below.
Compound No. 1:
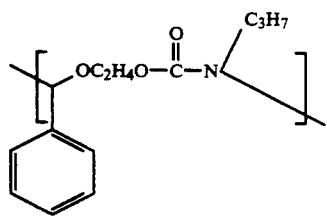
Compound No. 2:
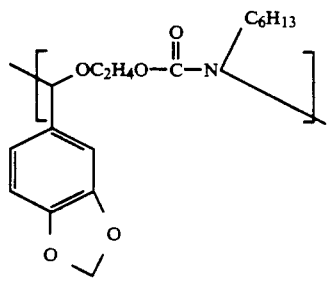
Compound No. 3:
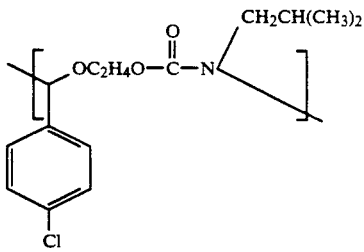
Compound No. 4:
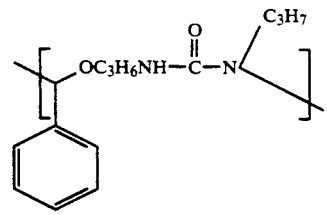
Compound No. 5:
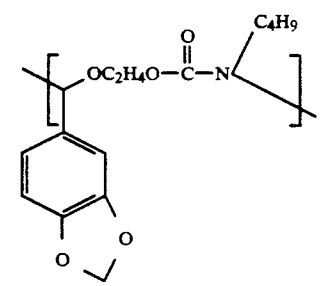
Compound No. 6:
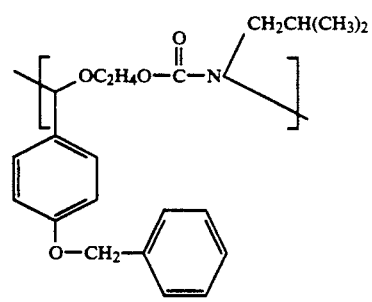
Compound No. 7:
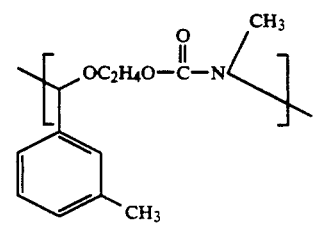
Compound No. 8:
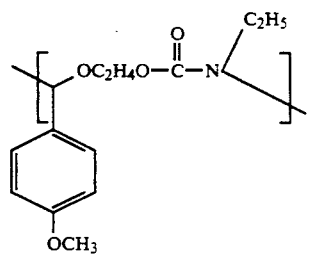
Compound No. 9:
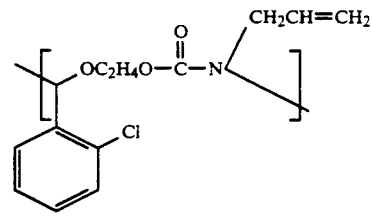
Compound No. 10:
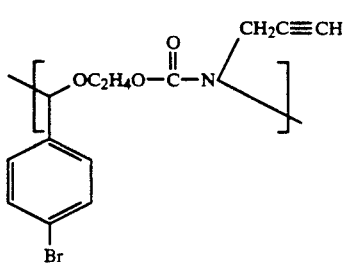
Compound No. 11:

-continued
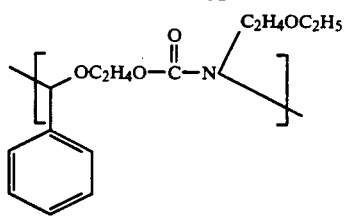
Compound No. 12:
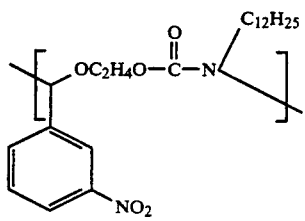
Compound No. 13:
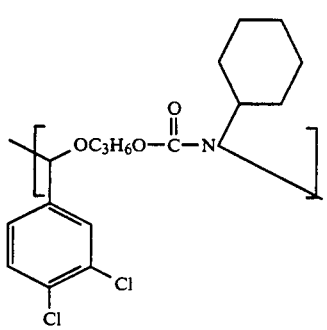
Compound No. 14:
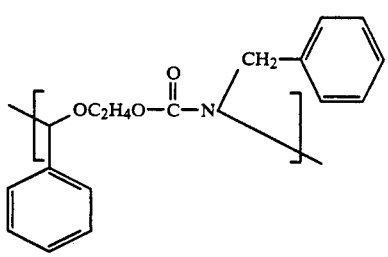
Compound No. 15:
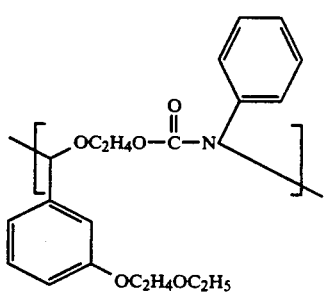
Compound No. 16:
-continued
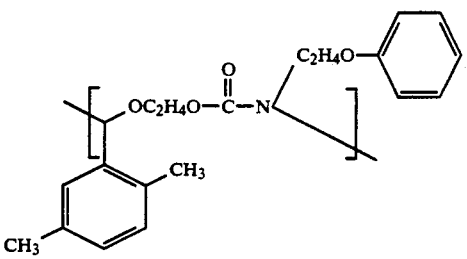
Compound No. 17:
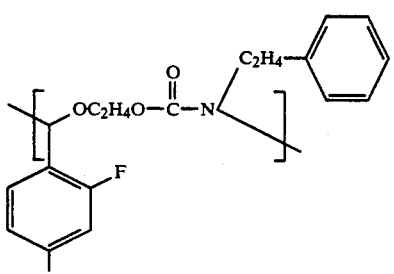
Compound No. 18:
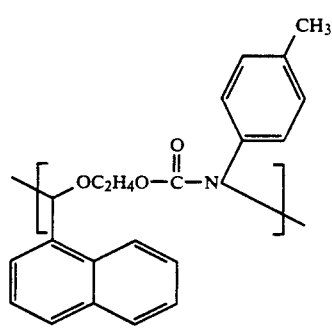
Compound No. 19:
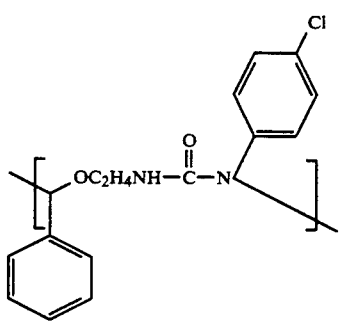
Compound No. 20

-continued
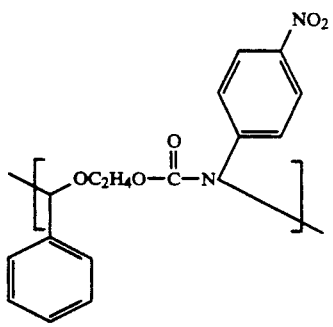
Compound No. 21:
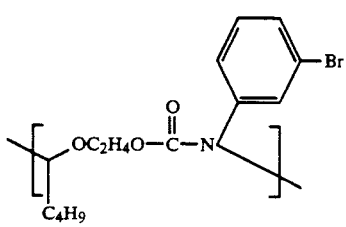
Compound No. 22:
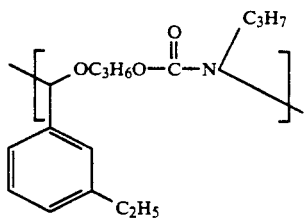
Compound No. 23:
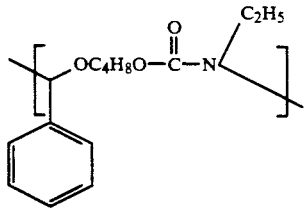
Compound No. 24:
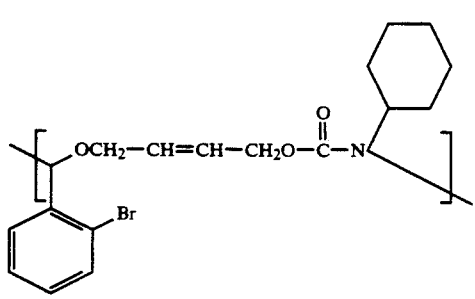
Compound No. 25:
-continued
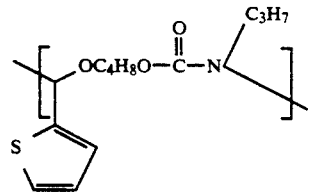
Compound No. 26:
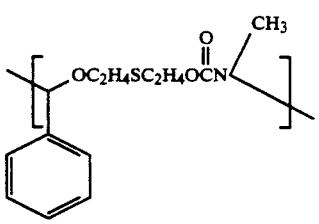
Compound No. 27:
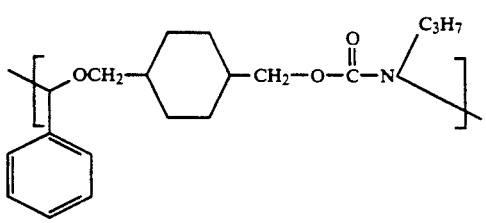
Compound No. 28:
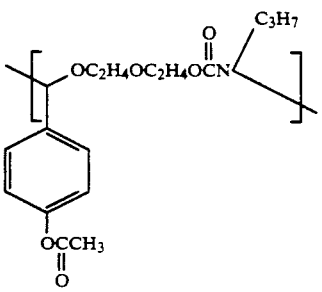
Compound No. 29:
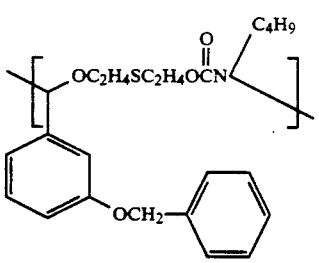
Compound No. 30:
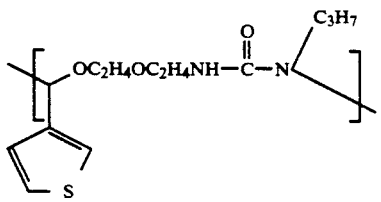

Further compounds of the formula I which have similarly favorable properties are summarized in the table below:

| No. | X     | R¹           | R²      | R³                  |
|-----|-------|--------------|---------|---------------------|
| 31  | O—CO  | $C_2H_4$     | $C_3H_7$ | $C_2H_5$            |
| 32  | CO    | $C_3H_6$     | $C_3H_7$ | $C_4H_9$            |
| 33  | O—CO  | $C_2H_4$     | $C_3H_7$ | $C_4H_9$            |
| 34  | O—CO  | $C_3H_6$     | $C_3H_7$ | $C_4H_9$            |
| 35  | NH—CO | $C_3H_6$     | $C_4H_9$ | $C_4H_9$            |
| 36  | NH—CO | $CH(CH_3)CH_2$ | $C_3H_7$ | $C_4H_9$          |
| 37  | O—CO  | $C_2H_4$     | $C_3H_6Cl$ | $C_4H_9$         |
| 38  | NH—CO | $C_3H_6$     | $C_3H_7$ | 4-Bromophenyl       |
| 39  | O—CO  | $C_2H_4$     | $C_3H_7$ | 4-Methoxyphenyl     |
| 40  | CO    | $C_3H_6$     | $C_3H_7$ | 4-Tolyl             |
| 41  | O—CO  | $C_4H_8$     | $C_4H_9$ | 2-Naphthyl          |
| 42  | NH—CO | $C_3H_6$     | $C_3H_7$ | 4-Nitrophenyl       |
| 43  | NH—CO | $C_2H_4$     | $C_3H_7$ | 3-Methoxyphenyl     |
| 44  | O—CO  | $C_3H_6$     | $C_3H_7$ | 3,4-Dichlorophenyl  |
| 45  | O—CO  | $C_2H_4$     | $C_3H_7$ | 2,6-Dichlorophenyl  |
| 46  | O—CO  | $CH(CH_3)CH_2$ | $C_3H_7$ | 2,4-Difluorophenyl |
| 47  | O—CO  | $C_3H_6$     | $C_3H_7$ | 2,3,4-Trichlorophenyl |
| 48  | O—CO  | $C_2H_4$     | $C_3H_7$ | Ferrocenyl          |

According to the invention, a positive-working radiation-sensitive mixture is also proposed which contains,
(a) a binder which is insoluble in water and soluble or at least swellable in aqueous alkaline solutions,
(b) a compound which generates a strong acid under the action of actinic radiation, and
(c) a compound which has at least one acid-cleavable C—O—C bond and whose acid cleavage products are more readily soluble in aqueous alkaline solutions than the compound itself.

In the mixture according to the invention, the acid-cleavable compound (c) comprises an oligomeric N,O-acetal of the formula I described above.

The radiation-sensitive mixture according to the invention is distinguished by a high sensitivity over a wide spectral range. It shows a high thermal stability and makes it possible to accurately reproduce even superfine structures of an original. This is due to the mixture providing an unusually high differentiation of the solubility between image areas and non-image areas.

The content of acid-cleavable material (c) in the radiation-sensitive mixture according to the invention can be varied depending on the intended use of the mixture and is generally between 1 to 60% by weight, preferably between 5 to 50% by weight, each relative to the total weight of the solids in mixture.

Photolytic acid donors b) are added to the acid-cleavable compounds c) contained in the radiation-sensitive mixture according to the invention. Any known acid donor or mixture of known acid donors can be used. Particularly, onium salts, such as diazonium, phosphonium, sulfonium and iodonium salts of non-nucleophilic acids, for example of $HSbF_6$, $HAsF_6$ or $HPF_6$ [described in J. V. Crivello, Polym. Eng. Sci., 23, 953 (1983)], halogen compounds (see EP-A 0,232,972, DE-A 1,572,089, DE-A 1,817,540, DE-A 1,949,010, U.S. Pat. No. 3,912,606 and DE-A 2,317,846), especially trichloromethyltriazine derivatives (see U.S. Pat. No. 3,515,552, U.S. Pat. No. 3,536,489, U.S. Pat. No. 3,779,778, DE-A 2,718,259, DE-A 3,337,024, DE-A 3,333,450, DE-A 2,306,248, DE-A 2,243,621 and DE-A 1,298,414) or trichloromethyloxadiazole derivatives (see DE-A 3,021,590, DE-A 3,021,599, DE-A 2,851,472, DE-A 2,949,396, DE-A 3,333,450 and EP-A 0,135,348), o-quinonediazidesulfochlorides or organometal/organohalogen combinations are suitable.

Although very good results are obtainable with such compounds, these are generally not preferred since acids having a highly corrosive action are generated in such radiation-sensitive mixtures. Rather, those photolytic acid donors are preferred which generate sulfonic acids on exposure. Examples of such compounds which may be mentioned are the $\alpha$-carbonyl-$\alpha$-sulfonyldiazomethanes, or $\alpha,\alpha$-bis-sulfonyldiazomethanes described in DE-A 3,930,087 and 3,930,086, nitrobenzyl sulfonates (described in F. M. Houlihan et al., J. Photopolym. Sci. Techn., 3, 259, 1990; T. Yamaoka et al., J. Photopolym. Sci. Techn., 3, 275, 1990), pyrogallol sulfonates [described in T. Ueno et al., Chemical Amplification Positive Resist Systems Using Novel Sulfonates as Acid Generators, in "Polymers for Microelectronics—Science and Technology", edited by Y. Tabata et al., Kodansha-Weinheim-New York, 1989, pages 66-67] or iminosulfonates (described in M. Shirai et al., J. Photopolym. Sci. Techn., 3, 301, 1990). The $\alpha$-pyridones containing N-sulfonyloxy groups mentioned in U.S. Ser. No. 07/870,920; filed Apr. 20, 1992, and U.S. Pat. No. 5,229,254; issued July, 1993 and U.S. Pat. No. 5,230,985; issued July, 1993, which correspond respectively to the German Applications P 41 12 967.9, P 41 12 966.0, and p 41 12 965.2, filed concomitantly, are particularly preferred. These latter three later docket numbers and applications are hereby incorporated by reference in their entireties.

The amount of (b) added depends on the intended use of the mixture. In general, 0.2 to 25% by weight, based on the weight of solids in the mixture of the photolytic acid donors, are added to the mixture. Proportions of 0.5 to 15% by weight are preferred, and 1 to 10% by weight is particularly preferred. These quantities can be fixed precisely only in a concrete formulation and differ from type to type. The photolytic acid donors preferably have absorption maxima in the region between 200 and 500 nm. Consequently, the spectral sensitivity of the mixtures according to the invention is thereby fixed, and they can be selected in such a way that sensitivities appropriate to practice can be obtained in the range of the technically important radiation sources, for example g-line (436 nm), i-line (365 nm) or UV2 (248 nm). The acid-cleavable compounds (c) which can be used according to the invention can then be selected in such a way that they have virtually no characteristic absorption in these ranges. By means of steps known to those skilled in the art, for example by spectral sensitization, the sensitivity range of the acid-donating compounds (b) can be further widened, so that even radiation sources in the visible region or in the short-wave region of X-ray radiation can be used. Finally, other radiation sources such as electron beams or ion beams, can also be used for the imagewise differentiation of the mixture according to the invention, especially if highly active acid donors are used, such as are described, for example, in EP-A 0,318,649.

If desired, other acid-cleavable compounds can be added to the mixtures according to the invention. Any known additional acid-cleavable compound can be used. The following compound classes have proven suitable:
(1) compounds having at least one orthocarboxylic acid ester group and/or carboxylic acid amide-acetal group, the compounds also having a polymeric character and it being possible for the said groupings to occur as linking elements in the main chain or as substituents in side chains (see DE-A 2,610,842 and 2,928,636), (2) oligomeric or polymeric compounds with recurring acetal and/or ketal groupings in the main chain (see DE-A 2,306,248 and 2,718,254), (3) compounds having at least one enol ether grouping or N-acyliminocarbonate grouping (see EP-A 0,006,626 and 0,006,627), (4) cyclic acetals or ketals of β-ketoesters or β-ketoamides (see EP-A 0,202,196), (5) compounds having silyl ether groupings (see DE-A 3,544,165 and 3,601,264), (6) compounds having silyl enol ether groupings (see DE-A 3,730,785 and 3,730,783), (7) monoacetals and monoketals, whose aldehyde or keto component respectively has a solubility of between 0.1 and 100 g/l in the developer (see DE-A 3,730,787), (8) ethers based on tertiary alcohols (see U.S. Pat. No. 4,603,101) and (9) carboxylic acid esters and carbonates of tertiary alcohols, allylic alcohols or benzylic alcohols [see U.S. Pat. No. 4,491,628 and J. M. Frechet et al., J. Imaging Sci. 30, 59–64 (1986)].

Mixtures of the said acid-cleavable compounds can also be used. However, acid-cleavable compounds are preferably used which are classified under one of the above-mentioned types (1) to (9) and, amongst these, especially those which have an acid-cleavable C—O—C bond. Amongst these, those compounds are particularly preferred which belong to the types (1), (2), (7) and (9). Under type (2) the polymeric acetals are especially preferred and, under the acid-cleavable compounds of type (7) those whose aldehyde or ketone component has a boiling point above 150° C., preferably above 200° C., are especially preferred. Overall, however, mixtures of these acid cleavable compounds and compounds of Formula I are not preferred.

The compound (c) or the combination of compounds (c) is preferably present in a concentration from 1 to 60% by weight, based on the total weight of solids in the mixture.

The radiation-sensitive mixture according to the invention also contains at least one polymeric binder which is insoluble in water but soluble or at least swellable in aqueous alkaline solutions. Any binder known in the art can be used which meets those requirements. The binder is distinguished in particular by being compatible with the other constituents of the radiation-sensitive mixture according to the invention and having the lowest possible characteristic absorption, i.e., high transparency, especially in the wavelength range from 190 to 550 nm.

Binders based solely on novolak condensation resins, which are generally used in combination with naphthoquinonediazides as the photoactive components, do not meet the requirements for use in the UV2 range. Although novolak condensation resins show, after imagewise exposure, an increase in the solubility in aqueous alkaline developers in the exposed areas, their characteristic absorption is undesirably high in the region of the short wavelength desired for the irradiation.

For applications in the UV2 range, however, binders containing novolak condensation resins admixed with other resins of higher transparency can be used. The mixing ratios here depend predominantly on the nature of the binder to be mixed with the novolak resin. Especially important factors are the degree of characteristic absorption of the binder in the said wavelength range, and the miscibility with the other constituents of the radiation-sensitive mixture. In general, however, the binder of the radiation-sensitive mixture according to the invention preferably contains at most 50% by weight, especially at most 20% by weight, of a novolak condensation resin when the mixture is to be irradiated with near UV light.

However, for conventional applications, i.e., with light sources in the near UV region, binders based on novolak condensation resins are particularly suitable which have generally been used in combination with naphthoquinone-diazides as the photoactive components. Such phenol/formaldehyde condensates have been described many times and can, as a phenolic component, contain phenol, the three position-isomeric cresols or other alkylphenols, for example xylenols, as components. Apart from formaldehyde, other aldehydes can also be utilized for preparing the polymer.

The polymers containing hydroxy groups, described below, can also be used for irradiations with near UV light, and these can be admixed with the novolak polymers described above in a proportion of up to 50%, preferably of up to 20%.

Suitable binders include homopolymers or copolymers of p-hydroxystyrene and homo and copolymers of alkyl derivatives thereof, for example of 3-methyl-4-hydroxystyrene, of 3,5-dimethyl-4-hydroxystyrene or 2,3-dimethyl-4-hydroxystyrene. Also useful are homopolymers or copolymers of other vinylphenols, for example of 2- or 3-hydroxystyrene or of 4-methyl-3-hydroxystyrene, or the esters or amides of methacrylic acid with phenols, for example pyrocatechol, resorcinol, hydroquinone, pyrogallol or aminophenols and the corresponding amides with aromatic amines. Polymerizable compounds such as styrene, methyl methacrylate, methyl acrylate or the like can be used as comonomers.

Mixtures having an increased plasma resistance are obtained when silicon-containing vinyl monomers, for example vinyltrimethyl-silane or allyltrimethylsilane, are used for the preparation of copolymers of the above type. The transparency of these binders is generally higher in the region of interest, so that improved structuring is possible.

Homopolymers or copolymers of maleimide can also be used. These binders too show a high transparency in the wavelength range described. Here again, the comonomers preferably used are styrene, substituted styrenes, vinylphenols, propenylphenols, vinyl ethers, vinyl esters, vinylsilyl compounds or (meth)acrylates.

Finally, copolymers of styrene can be used with comonomers which effect an increase in solubility in aqueous alkaline solutions. These include, for example, maleic anhydride, maleic acid half-esters or the like.

The said binders can also be mixed with one another if this does not impair the film forming properties and the optical quality of the radiation-sensitive mixture.

The quantity of binder can be varied depending on the intended use of the mixture, and is in general 40 to 95% by weight, especially 40 to 90% by weight, preferably 50 to 85% by weight, relative to the total weight of solids in the radiation-sensitive mixture.

The extinction of the binder or of the combination of binders (a) in the wavelength range of the sensitivity of compound (b) is preferably less than 0.5 $\mu m^{-1}$.

If appropriate, one or more of dyes, pigments, plasticizers, wetting agents, flow agents, polyglycols and cellulose ethers, for example, ethylcellulose, can also be added to the radiation-sensitive mixtures according to the invention to improve special requirements, such as flexibility, adhesion and gloss.

Any known substrate can be coated in any known manner with the radiation-sensitive mixture according to the invention. When a substrate is to be coated, the radiation-sensitive mixture according to the invention is expediently dissolved in a solvent or in a combination of solvents. Ethylene glycol, ethylene glycol monomethyl ether, ethylene glycol dimethyl ether, ethylene glycol monoethyl ether or propylene glycol monoalkyl ethers, especially propylene glycol methyl ether, aliphatic esters (for example ethyl acetate, hydroxyethyl acetate, alkoxyethyl acetate, n-butyl acetate, propylene glycol alkyl etheracetate, especially propylene glycol methyl ether-acetate or amyl acetate), ethers (for example dioxane), ketones (for example methyl ethyl ketone, methyl isobutyl ketone, cyclopentanone and cyclohexanone), dimethylformamide, dimethylacetamide, hexamethylphosphoramide, N-methylpyrrolidone, butyrolactone, tetrahydrofuran and mixtures thereof are particularly suitable for this purpose. Glycol ethers, aliphatic esters and ketones are particularly preferred.

Ultimately, the choice of the solvents depends on the coating process used, on the desired layer thickness and on the drying conditions. The solvents must also be chemically neutral, i.e., they must not react irreversibly with the other layer components.

The solution prepared with the said solvents generally has a solids content from 5 to 60% by weight, preferably up to 50% by weight.

The invention also relates to a radiation-sensitive recording material which comprises a substrate and, preferably located thereon, a radiation-sensitive layer of the radiation-sensitive mixture according to the invention.

Possible substrates are all those materials of which capacitors, semiconductors, multi-layer printed circuits or integrated circuits are composed or from which these can be produced. Silicon substrates which can also be thermally oxidized and/or coated with aluminum, and also doped merit special mention. In addition, all other substrates usual in semiconductor technology are possible, such as silicon nitride, gallium arsenide and indium phosphide. Moreover, the substrates known from liquid crystal display manufacture are possible, such as, for example, glass and indium-tin oxide and also metal plates and foils, for example foils of aluminum, copper and zinc, bimetal foils and trimetal foils, and also electrically non-conductive foils on which metals have been vapor-deposited, and paper. These substrates can have been thermally-pretreated, superficially roughened, incipiently etched or pretreated with chemicals to improve desired properties, for example to enhance the hydrophilic character.

To impart better cohesion and/or better adhesion of the radiation-sensitive layer to the substrate surface, the layer can contain an adhesion promoter. In the case of silicon or silica substrates, adhesion promoters of the aminosilane type such as, for example, 3-aminopropyl-triethoxysilane or hexamethyldisilazane, can be used for this purpose. Also, a layer containing an adhesion promoter can be applied to the substrate prior to application of the radiation-sensitive mixture.

Suitable supports for the production of photomechanical recording layers, such as printing forms for letterpress printing, planographic printing, screen printing and flexographic printing, are in particular aluminum plates which may have been anodically oxidized, grained and/or silicated beforehand, zinc and steel plates which may be chromium-plated, and plastic films and paper.

The recording material according to the invention is exposed imagewise to actinic radiation. Within the scope of this description, actinic radiation is to be understood as any radiation having an energy at least corresponding to that of short-wave visible light. Suitable radiation sources are especially metal halide lamps, carbon arc lamps, xenon lamps and mercury vapor lamps. Likewise, exposure can be carried out with high-energy radiation such as laser radiation, electron beams or X-rays. However, lamps which can emit light of a wavelength from 190 to 260 nm, i.e., especially xenon lamps and mercury vapor lamps, are particularly preferred. Furthermore, laser light sources can also be used, for example excimer lasers, especially KrF or ArF lasers, which emit at 248 and 193 nm respectively. The radiation sources must show adequate emission in the said wavelength ranges.

The thickness of the light-sensitive layer depends on the intended use. In general it is between 0.1 and 100 $\mu$m, preferably between 1 and 10 $\mu$m.

The invention also relates to a process for producing a radiation-sensitive recording material. The radiation-sensitive mixture can be applied to the substrate by any known process such as spraying, flow-coating, rolling, whirler-coating and dip-coating. The solvent is then removed by evaporation, so that the radiation-sensitive layer remains on the surface of the substrate. The removal of the solvent can be promoted by heating the layer to temperatures of up to 150° C. The mixture can, however, also be first applied in the above-mentioned way to a temporary support, from which it is transferred under pressure and at an elevated temperature to the final support material. The materials used as temporary support can in principle be all those which are also suitable as support materials. Subsequently, the layer is irradiated imagewise. The layer is then treated with a developer solution which dissolves and removes the irradiated areas of the layer, so that an image of the original used in the imagewise irradiation remains on the substrate surface.

Any known developer can be used. Suitable developers are especially aqueous solutions which contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP-A 0,062,733, U.S. Pat. No. 4,628,023, U.S. Pat. No. 4,141,733, EP-A 0,097,282 and EP-A 0,023,758. The content of these substances in the developer solution is in general 0.1 to 15% by weight, preferably 0.5 to 5% by weight, relative to the weight of the developer solution. Preferably, metal ion-free developers are used. Small quantities of a wetting agent can have been added to the developers, in order to facilitate the detachment of the soluble areas of the layer.

The developed layer structures can be post-hardened. This is effected in any known manner, in general by heating on a hotplate up to a temperature below the flow temperature and subsequent exposure of the whole area to the UV light from a xenon-mercury vapor lamp (range from 200 to 250 nm). As a result of the post-hardening, the image structures are crosslinked, so that in general they have a flow resistance up to temperatures of more than 200° C. The post-hardening can also be effected without a temperature increase solely by irradiation with high-energy UV light.

The radiation-sensitive mixture according to the invention may be used in the production of integrated circuits or of individual electronic components by lithographic processes. The developed resist layer here serves as a mask for the subsequent process steps. Examples of such steps are the etching of the layer support, the implantation of ions in the layer support or the precipitation of metals or other materials on the layer support.

Examples 1–17 and 22–27, which follow illustrate the suitability of the mixture according to the invention for recording materials in microlithography using radiation of very diverse energy. The superiority of the mixtures according to the invention over the state of the art is demonstrated by reference to the comparison examples 18–21. Examples 28–30 document the applicability of the mixture in printed circuits and planographic printing plates.

In the examples, the quantities are as a rule stated as parts by weight (p.b.w.). Unless otherwise stated, percentage figures and quantitative ratios are to be understood as being in weight units.

EXAMPLE 1

A coating solution was prepared from
7.5 p.b.w. of a cresol/formaldehyde novolak having a softening range from 105° to 120° C.,
2.0 p.b.w. of Compound 1 and
0.6 p.b.w. of α,α-bis(4-tert.-butyl-benzenesulfonyl)-diazomethane in
42 p.b.w. of propylene glycol monomethyl ether-acetate.

The solution was filtered through a filter of 0.2 $\mu m$ pore diameter and whirler-coated at 3,200 rpm onto a wafer treated with an adhesion promoter (hexamethyldisilazane). After drying for 1 minute at 100° C. on a hotplate, a layer thickness of 1.1 $\mu m$ was obtained.

The recording material was exposed imagewise under an original to the radiation of a xenon-mercury vapor lamp at 365 nm with an energy of 80 mJ/cm$^2$. To complete the cleavage of the solution inhibitor, the material was heated for 1 minute to 60° C.

The recording material was developed using a developer of the following composition:
5.3 p.b.w. of sodium metasilicate×9 H$_2$O,
3.4 p.b.w. of trisodium phosphate×12 H$_2$O,
0.3 p.b.w. of sodium dihydrogen phosphate and
191 p.b.w. of deionized water.

After a developing time of 60 seconds, this gave a defect-free image of the mask with steep resist flanks. Structures of <0.55 were resolved in true detail. An examination of the flanks of the resist profiles by means of scanning electron microscopy proved that these were aligned virtually perpendicular to the substrate surface. The contrast was 3.8.

The contrast of a positive resist, $\gamma_p$ is defined as $$\gamma_p = 1 / (\log D_p - \log D_p^0) = [\log(D_p/D_p^0)]^{-1}$$

where $D_p^0$ is the irradiation dosage at which the developer starts to attack the exposed film, and $D_p$ is the resist space point (=resist sensitivity). An accurate description of this parameter has been given in the article by L. F. Thompson and M. J. Bowden "Resist Processing" (Introduction to Microlithography, Theory, Materials and Processing, edited by C. G. Willson, L. F. Thompson and M. J. Bowden, ACS Symp. Ser., 219, 164 et seq. (1983), American Chemical Society, Washington).

EXAMPLE 2

A coating solution was prepared from
7.5 p.b.w. of a styrene/p-hydroxystyrene copolymer (molar ratio 20:80) having a mean molecular weight of 32,000,
2.0 p.b.w. of Compound 2 and
0.5 p.b.w. of α,α-bis-(4-tert.-butylbenzenesulfonyl)-diazomethane in
42 p.b.w. of propylene glycol monomethyl ether-acetate.

The solution was filtered through a filter of 0.2 $\mu m$ pore diameter and whirler-coated at 3,000 rpm onto a wafer treated with an adhesion promoter (hexamethyldisilazane). After drying for 1 minute at 100° C. on a hot plate, a layer thickness of 1.12 $\mu m$ was obtained.

The recording material was exposed imagewise under an original to the radiation of a xenon-mercury vapor lamp at 260 nm with an energy of 92 mJ/cm$^2$ and then heated for 1 minute at 65° C. It was then processed using an aqueous developer which contained 2.38% of tetramethylammonium hydroxide. After 60 seconds, this gave a defect-free image of the mask with high flank stability. A contrast value of 5.6 was determined, and here again structures of <0.55 $\mu m$ were resolved in true detail.

EXAMPLE 3

A coating solution was prepared from
7.5 p.b.w. of a poly(pyrocatechol monomethacrylate) having a softening range from 125° to 135° C.,
2.0 p.b.w. of Compound 3 and
0.4 p.b.w. of 2-(4-ethoxy-naphthalen-1-yl)-4,6-bis-trichloromethyl-1,3,5-triazine in
42 p.b.w. of propylene glycol monomethyl ether-acetate.

The solution was filtered through a filter of 0.2 $\mu m$ pore diameter and whirler-coated at 3,200 rpm onto a wafer treated with an adhesion promoter (hexamethyldisilazane). After drying for 1 minute at 100° C. on a hot plate, a layer thickness of 1.1 $\mu m$ was obtained.

A wafer coated in this way was irradiated under an original with light of a wavelength of 405 nm and an energy of 100 mJ/cm$^2$. The material was then heated for 1 minute at 60° C. After development, an image true to the original was obtained.

EXAMPLE 4

The experiment of Example 3 was repeated, but light of a wavelength of 436 nm was used. To obtain a sharp-edged image of the original, it was necessary to use an exposure energy of 135 mJ/cm$^2$.

EXAMPLE 5

A coating solution was prepared from
20 7.5 p.b.w. of a styrene/maleimide copolymer (molar ratio 1:1) having a softening range from 165° to 180° C.,
0.6 p.b.w. of benzenesulfonyl-(4-chlorobenzoyl)-diazomethane in
42 p.b.w. of propylene glycol monomethyl ether-acetate.

The solution was filtered through a filter of 0.2 $\mu m$ pore diameter and whirler-coated at 3,700 rpm onto a wafer treated with an adhesion promoter (hexamethyldisilazane). After drying for 1 minute at 100° C., a layer thickness of 0.98 μm was obtained.

The recording material was exposed imagewise under an original to the radiation of a xenon-mercury vapor lamp at 260 nm with an energy of 120 mJ/cm². The material was then heated for 2 minutes at 65° C.

The recording material was developed using a 0.02N aqueous solution of tetramethylammonium hydroxide, and the exposed areas were detached without residue within 60 seconds. A defect-free image of the mask with steep resist flanks was obtained. The loss in the dark was <20 nm; even structures of <0.6 μm were resolved in true detail.

EXAMPLE 6

A coating solution was prepared from
7.5 p.b.w. of the copolymer from Example 5,
2.0 p.b.w. of Compound 4 and
0.4 p.b.w of 4-(2-[2]furyl-vinyl)-6-trichloromethyl-2-pyrone in
42 p.b.w. of propylene glycol monomethyl ether-acetate.

The solution was filtered through a filter of 0.2 μm pore diameter and whirler-coated at 3,500 rpm onto a wafer treated with an adhesion promoter (hexamethyldisilazane). After drying for 1 minute at 100° C., a layer thickness of 1.00 μm was obtained.

The recording material was exposed imagewise under an original to radiation from a xenon-mercury vapor lamp at 260 nm with an energy of 112 mJ/cm² and then heated for 1 minute at 60° C.

The recording material was developed using a 0.02N aqueous solution of tetramethylammonium hydroxide. The exposed areas were detached without residue within 60 seconds and an image of the original true to detail was obtained. The measured contrast was about 8; the edge steepness of the image was correspondingly excellent.

EXAMPLE 7

A coating solution was prepared from
7 5 p.b.w. of the copolymer described in Example 2,
2.0 p.b.w. of Compound 11 and
0.3 p.b.w. of triphenylsulfonium trifluoromethanesulfonate in
42 p.b.w. of propylene glycol monomethyl ether-acetate.

The solution was filtered through a filter of 0.2 μm pore diameter and whirler-coated at 3,500 rpm onto a wafer treated with an adhesion promoter (hexamethyldisilazane). After drying for 1 minute at 100° C., a layer thickness of 1.04 μm was obtained.

The recording material was exposed imagewise under an original to radiation from a xenon-mercury vapor lamp at 260 μm with an energy of 112 mJ/cm². It was then heated for 1 minute at 60° C.

The recording material was developed using a 0.27N aqueous solution of tetramethylammonium hydroxide. The exposed areas were detached without residue within 60 seconds and an image of the original true to detail was obtained. Lines and gaps down to 0.5 μm were reproduced true to the mask.

EXAMPLE 8

The recording material from Example 7 was irradiated with synchrotron radiation (BESSY, Berlin, 754 MeV) through a gold-on-silicon mask at a dosage of 120 mJ/cm². The experimental arrangement is to be found in A. Heuberger, Microelectr. Eng., 3, 535 (1985). The exposed material was left to lie for 30 minutes at room temperature. After development using the developer described in Example 7 and a developing time of 120 seconds, a defect-free image of the mask down to structures of <0.4 μm was obtained. The contrast was determined to be >8; the resist flanks were virtually perpendicular to the planar substrate surface.

EXAMPLE 9

A coating solution was prepared from
7.5 p.b.w. of a formaldehyde/m-kresol/p-kresol novolak having a softening point from 100° to 110° C.,
2.0 p.b.w. of Compound 14 and
0.3 p.b.w. of 2-(4-methoxystyryl)-4,6-bis-trichloromethyl-1,3,5-triazine in
42 p.b.w. of propylene glycol monomethyl ether-acetate.

The solution was filtered through a filter of 0.2 μm pore diameter and whirler-coated at 3,200 rpm onto a wafer treated with an adhesion promoter (hexamethyldisilazane). After drying for 1 minute at 100° C., a layer thickness of 1.05 μm was obtained.

The recording material was exposed imagewise under an original to radiation of a wavelength of 365 nm with an energy of 95 mJ/cm² and then heated for 1 minute at 65° C.

The recording material was developed using a developer of the following composition:
5.5 p.b.w. of sodium metasilicate×9 H₂O,
3.4 p.b.w. of trisodium phosphate×12 H₂O, and
0.4 p.b.w. of anhydrous monosodium phosphate in
90.7 p.b.w. of deionized water,
The exposed areas were detached without residue within 60 seconds and an image of the original true to detail was obtained. Lines and gaps down to 0.5 μm were reproduced true to the mask.

EXAMPLE 10

A coating solution was prepared from
6.0 p.b.w. of a homopolymer of 3-methyl-4-hydroxystyrene having a softening point from 155° to 160° C. and a molecular weight of 22,000,
3.5 p.b.w. of Compound 1 and
0.1 p.b.w. of 1,2,3-tris-methanesulfonyloxybenzene in
42 p.b.w. of propylene glycol monomethyl ether-acetate.

The solution was filtered through a filter of 0.2 μm pore diameter and whirler-coated at 3,000 rpm onto a wafer treated with an adhesion promoter (hexamethyldisilazane). After drying for 1 minute at 100° C., a layer thickness of 1.05 μm was obtained.

The recording material was exposed imagewise under an original to radiation of a wavelength of 248 nm with an energy of 25 mJ/cm². The recording material was then heated for 1 minute at 60° C.

The recording material was developed using an aqueous developer which contained 2.38% of tetramethylammonium hydroxide. After only a few seconds, it was possible to obtain an image true to the original in which even details of <0.5 μm were resolved. The contrast was determined to be 4.5.

EXAMPLE 10a 5 wafers were coated as described in Example 10 but in place of the quantity of Compound 1 indicated therein, 0.3, 0.6, 0.9, 1.2 and 1.5 p.b.w. were used. The samples were processed as described in Example 10. The results are shown in the tables which follow Comparison Example 21.

EXAMPLE 11

The mixture described in Example 10 was applied, exposed and finally heated as described therein. The development was carried out using the developer described therein, to which 10% of isopropanol had been added. Details down to 0.3 μm were reproduced true to the original. The profiles of even the smallest fractures were virtually vertical.

EXAMPLE 12

A coating solution was prepared from
6.0 p.b.w. of the homopolymer indicated in Example 10,
3.5 p.b.w. of Compound 1 and
0.2 p.b.w. of 4-methyl-6-(4-methoxystyryl)-N-methanesulfonyloxy-α-pyridone in
42 p.b.w. of propylene glycol monomethyl ether-acetate.

The solution was filtered through a filter of 0.2 μm pore diameter and whirler-coated at 3,100 rpm onto a wager treated with an adhesion promoter (hexamethyldisilazane). After drying for 1 minute at 100° C., a layer thickness of 1.05 μm was obtained.

The recording material was exposed imagewise under an original to the radiation of a KrF-excimer laser at 248 nm with an energy of 65 mJ/cm$^2$. The recording material was then heated for 1 minute at 60° C.

The recording material was developed using an aqueous developer which contained 2.38% of tetramethylammonium hydroxide. After only a few seconds, it was possible to obtain an image true to the original, in which even details of less than 0.5 μm were resolved.

EXAMPLE 13

The material described in Example 12 was irradiated with light of a wavelength of 240 to 260 nm and further processed as described therein. In order to obtain a true image of the original down to 0.6 μm, a dosage of 45 mJ/cm$^2$ was necessary.

EXAMPLE 14

The material described in Example 12 was irradiated with light of a wavelength of 365 nm and further processed as described therein. In order to obtain a true image of the original down to 0.6 μm, a dosage of 85 mJ/cm$^2$ was necessary.

EXAMPLE 15

The material described in Example 12 was irradiated with light of a wavelength of 405 nm and further processed as described therein. In order to obtain a true image of the original down to 0.65 μm, a dosage of 97 mJ/cm$^2$ was necessary.

EXAMPLE 16

The material described in Example 12 was irradiated with light of a wavelength of 436 nm and further processed as described therein. In order to obtain a true image of the original down to 0.65 μm, a dosage of 122 mJ/cm$^2$ was necessary.

EXAMPLE 17 AND COMPARISON EXAMPLES 18 TO 21

In each case five coating solutions of the five basic formulations identified below were prepared. The solution inhibitor was employed in a quantity of 5% by weight, 10% by weight, 15% by weight, 20% by weight and 25% by weight, relative to the quantity of the polymer used (x=0.3 p.b.w., 0.6 p.b.w., 0.9 p.b.w., 1.2 p.b.w., 1.5 p.b.w.):

EXAMPLE 17

6.0 p.b.w. of the homopolymer indicated in Example 10,
x p.b.w. of Compound 1 and
0.2 p.b.w. of 2-(4-methoxystyryl)-4,6-bis-trichloromethyl-1,3,5-triazine in
42 p.b.w. of propylene glycol monomethyl ether-acetate.

COMPARISON EXAMPLE 18

6.0 p.b.w. of the homopolymer indicated in Example 10,
x p.b.w. of a monomeric acetal prepared from 1 mol of benzaldehyde and 2 mol of phenoxyethanol and
0.2 p.b.w. of 2-(4-methoxystyryl)-4,6-bis-trichloromethyl-1,3,5-triazine in
42 p.b.w. of propylene glycol monomethyl ether-acetate.

COMPARISON EXAMPLE 19

6.0 p.b.w. of the homopolymer indicated in Example 10,
x p.b.w. of an oligomeric acetal prepared from 1 mol of benzaldehyde and mol of diethylene glycol and
0.2 p.b.w. of 2-(4-methoxystyryl)-4,6-bis-trichloromethyl-1,3,5-triazine in
42 p.b.w. of propylene glycol monomethyl ether-acetate.

COMPARISON EXAMPLE 20

6.0 p.b.w. of the homopolymer indicated in Example 10,
x p.b.w. of an oligomeric acetal from 1 mol of benzaldehyde and 1 mol of butyne-1,4-diol and
0.2 p.b.w. of 2-(4-methoxystyryl)-4,6-bis-trichloromethyl-1,3,5-triazine in
42 p.b.w. of propylene glycol monomethyl ether-acetate.

COMPARISON EXAMPLE 21

6.0 p.b.w. of the homopolymer indicated in Example 10,
x p.b.w. of a monomeric acetal prepared from 1 mol of benzaldehyde with 2 mol of 1,4-bishydroxymethyl-cyclohexane and
0.2 p.b.w. of 2-(4-methoxystyryl)-4,6-bis-trichloromethyl-1,3,5-triazine in
42 p.b.w. of propylene glycol monomethyl ether-acetate.

The solutions were filtered through a filter of 0.2 μm pore diameter and each whirler-coated onto two wafers treated with an adhesion promoter (hexamethyldisilazane). The conditions were selected so that a layer thickness of 1.00±0.05 μm was obtained after drying at 100° C.

The wafers were then dipped for 1 minute at 21° C. into an aqueous developer containing 0.27 mol/l of tetramethylammonium hydroxide, and the layer loss was determined by means of a layer thickness-measuring instrument. The pure polymer had a loss rate of 327 nm/minute in this developer. The following values were obtained for the rates of loss in the dark from the various mixtures (nm/minute):

| Example No. | Concentration of solution inhibitor | | | | |
|---|---|---|---|---|---|
| | 5% | 10% | 15% | 20% | 25% |
| 10 | 103 | 39 | 6 | 8 | 6 |
| 17 | 92 | 45 | 10 | 10 | 8 |
| 18 | 370 | 225 | 157 | 143 | 182 |
| 19 | 340 | 309 | 299 | 266 | 287 |
| 20 | 192 | 152 | 96 | 107 | 163 |
| 21 | 197 | 145 | 114 | 97 | 65 |

It can be seen from this result that the oligomeric N,O-acetals according to the invention show a significantly improved inhibiting effect for polyhydroxystyrene polymers. Similar results could also be obtained with other phenolic polymers.

The remaining wafers were then irradiated by a KrF excimer laser at a dosage of 100 mJ/cm², heated for 1 minute at 60° C., and the loss in bright light was determined (nm/minute) as indicated below:

| Example No. | Concentration of solution inhibitor | | | | |
|---|---|---|---|---|---|
| | 5% | 10% | 15% | 20% | 25% |
| 10 | 450 | 600 | 780 | 900 | 977 |
| 17 | 412 | 450 | 617 | 822 | 897 |
| 18 | 470 | 521 | 640 | 842 | 912 |
| 19 | 320 | 350 | 345 | 375 | 360 |
| 20 | 400 | 510 | 590 | 690 | 820 |
| 21 | 420 | 478 | 534 | 590 | 700 |

This shows that the mixtures containing the N,O-acetals according to the invention have a very good dissolution-promoting action after exposure. The ratio of the loss rates between exposed and unexposed layer areas is in their case by far the greatest of all the examples, i.e., they allow a very good differentiation between image areas and non-image areas.

EXAMPLE 22

A coating solution was prepared from 7.5 p.b.w. of a copolymer of 3-methyl-4-hydroxystyrene/4-hydroxystyrene (molar ration 2:1) having a mean molecular weight of 18,000, 2.0 p.b.w. of Compound 1 (molecular weight approx. 3,000), 0.2 p.b.w. of α,α-bis-(4-methylbenzenesulfonyl)-diazomethane in 42 p.b.w. of propylene glycol monomethyl ether-acetate.

The solution was filtered through a filter of 0.2 μm pore diameter and whirler-coated at 3,200 rpm onto a wafer treated with an adhesion promoter (hexamethyldisilazane). After drying for one minute on a hot plate a layer thickness of 1.03 μm was obtained.

The recording material was exposed imagewise under an original to the radiation of a KrF-excimer laser with an energy of 34 mJ/cm², using a PAS 5000/70 exposure apparatus (manufacturer ASM-Lithography) and then heated for 1 minute at 60° C.

The recording material was developed using an aqueous developer which contained 2.38% of tetramethylammonium hydroxide. After 60 seconds a flawless reproduction of the mask was obtained, and structures down to 0.35 μm were resolved in true detail.

EXAMPLE 23

A coating solution was prepared from 7.5 p.b.w. of a copolymer of 3-methyl-4-hydroxystyrene/4-hydroxystyrene (molar ratio 1:1) having a mean molecular weight of 17,000, 2.0 p.b.w. of Compound (molecular weight approx. 5,000), 0.3 p.b.w. of α,α-bis-(4-chlorobenzenesulfonyl)-diazomethane in 42 p.b.w. of propylene glycol monomethyl ether-acetate.

The solution was filtered through a filter of 0.2 μm pore diameter and whirler-coated at 3,500 rpm onto a wafer treated with an adehsion promoter (hexamethyldisilazane). After drying for one minute on a hot plate a layer thickness of 0.98 μm was obtained.

The recording material was exposed imagewise under an original to the radiation of a KrF-excimer laser with an energy of 38 mJ/cm², using a PAS 5000/70 exposure apparatus (manufacturer ASM-Lithography) and then heated minute at 60° C.

The recording material was developed using an aqueous developer which contained 2.38% of tetramethylammonium hydroxide. After 60 seconds a flawless reproduction of the mask was obtained, in which even structures down to 0.30 μm were resolved in true detail. The angle of structure edges was in the range of 90°±3°.

EXAMPLE 24

A coating solution was prepared from 4.5 p.b.w. of a homopolymer of 3-methyl-4-hydroxystyrene having a mean molecular weight of 22,000.

3.0 p.b.w. of a homopolymer of 4-hydroxystyrene having a mean molecular weight of 30,000 (PHS from HOECHST CELANESE CORPORATION), 2.0 p.b.w. of Compound (molecular weight approx. 5,000), 0.3 p.b.w. of α,α-bis-(4-bromobenzenesulfonyl)-diazomethane in 42 p.b.w. of propylene glycol monomethyl ether-acetate.

The solution was filtered through a filter of 0.2 μm pore diameter and whirler-coated at 3,500 rpm onto a wafer treated with an adhesion promoter (hexamethyldisilazane). After drying for one minute on a hot plate a layer thickness of 0.94 μm was obtained.

The recording material was exposed imagewise under an original to the radiation of a KrF-excimer laser with an energy of 30 mJ/cm², using a PAS 5000/70 exposure apparatus (manufacturer ASM-Lithography) and then heated for 1 minute at 60° C.

The recording material was developed using an aqueous developer which contained 2.38% of tetramethylammonium hydroxide. While the non-image areas showed an erosion of <20 nm/min, the erosion produced by the developer in the exposed areas was >10,000 nm/min. After 60 seconds, a flawless reproduction of the mask was again obtained, and structures down to 0.30 μm were resolved in true detail. The angle of the structure edges was in the range of 90°±3°.

EXAMPLE 25

A coating solution was prepared from 3 0 p.b.w. of a homopolymer of 3-methyl-4-hydroxystyrene having a mean molecular weight of 22,000, 4.5 p.b.w. of a homopolymer of 4-hydroxystyrene having a mean molecular weight of 30,000 (PHS from HOECHST CELANESE CORPORATION), 2.0 p.b.w. of Compound (molecular weight approx. 5,000), 0.3 p.b.w. of α,α-bis-(4-chlorobenzenesulfonyl)-diazomethane in 42 p.b.w. of propylene glycol monomethyl ether-acetate.

The solution was filtered through a filter of 0.2 μm pore diameter and whirler-coated at 3,500 rpm onto a wafer treated with an adhesion promoter (hexamethyldisilazane). After drying for one minute on a hot plate a layer thickness of 0.90 μm was obtained.

The recording material was exposed imagewise under an original to the radiation of a KrF-excimer laser with an energy of 30 mJ/cm$^2$, using a PASW 5000/70 exposure apparatus (manufacturer ASM-Lithography) and then heated for 1 minute at 60° C.

The recording material was developed using an aqueous developer which contained 2.38% of tetramethylammonium hydroxide. While the non-image areas showed an erosion of <20 nm/min, the erosion produced by the developer in the exposed areas was >10,000 nm/min. After 60 seconds a flawless reproduction of the mask was obtained, structures down to 0.35 μm being resolved in true detail. The angle of the sturcutre edges was in the range of 90°±3°.

EXAMPLE 26

The coated wafer of Example 23 was exposed through a phase-shifting mask, using the exposure apparatus therein described. Under the conditions described in this example, structures down to 0.16 μm could be reproduced true to scale and with virtually vertical resist profiles.

EXAMPLE 27

The coated wafer of Example 24 was exposed through a phase-shifting mask, using the exposure apparatus therein described. Under the conditions described in this example, structures down to 0.16 μm could be reproduced true to scale and with virtually vertical resist profiles.

EXAMPLE 28

To produce an offset printing plate, an aluminum foil having a mechanically roughened and anodized surface was whirler-coated with a coating solution of the following composition:

7.5 p.b.w. of the novolak indicated in Example 1,
2.3 p.b.w. of Compound 1,
0.3 p.b.w. of 2-(4-methoxystyryl)-4,6-bis-trichloromethyl-1,3,5-triazine and
0.05 p.b.w. of crystal violet base in
90 p.b.w. of propylene glycol monomethyl ether-acetate.

After the layer was dried (dry weight about 2.5 g/cm$^2$), it was exposed under a positive test original for 30 seconds, stored for 15 minutes at room temperature and developed using a developer of the following composition:

0.5 p.b.w. of sodium hydroxide,
0.8 p.b.w. of sodium metasilicate×9 H$_2$O and
1.0 p.b.w. of 2-n-butoxyethanol in
97.7 p.b.w. of deionized water.

After rinsing with water, the plate was made ready for treating by wiping it with 1% phosphoric acid. After clamping it into a printing press, 55,000 perfect prints of the original were obtained.

EXAMPLE 29

The solution of a positive dry resist was prepared by preparing the following composition:

12.5 p.b.w. of the novolak described in Example 9,
10.0 p.b.w. of Compound 7,
0.5 p.b.w. of 4-(2-[2]furyl-vinyl)-6-trichloromethyl-2-pyrone and
0.1 p.b.w. of crystal violet in
25 p.b.w. of butanone.

A 25 μm thick polyethylene terephthalate film was coated with this solution to give a dry layer thickness of 16 μm. The surface of the dry resist film was laminated to a further polyethylene terephthalate film having lower adhesion. After peeling off the cover film, the dry film was laminated under pressure and heat to a brass plate. After cooling and peeling off the support film, the plate was exposed through an original, and good image contrast was visible. After storage for 20 minutes, the exposed areas were spray-developed using a developer of the composition indicated in Example 11. The plate was then etched through to smooth flanks. The milled products obtained can be yet further processed before they are separated.

EXAMPLE 30

A coating solution was prepared from 7.5 p.b.w. of the novolak indicated in Example 9,
2.0 p.b.w. of Compound 14,
0.05 p.b.w. of crystal violet base and
0.6 p.b.w. of 2-(4-methoxystyryl)-4,6-bis-trichloromethyl-1,3,5-triazine in
42 p.b.w. of propylene glycol monomethyl ether-acetate.

The solution was whirler-coated onto an electrolytically roughened and anodized aluminum plate which had been treated beforehand with an aqueous solution of polyvinylphosphonic acid, and dried. The layer weight of the dried layer was 1.5 μm. The imagewise exposure was carried out under a 5 kW metal halide lamp at a distance of 110 cm. After a waiting time of 10 minutes, the plate was developed using the developer described in Example 9, and the exposed areas were detached. The printing form thus obtained was gummed and clamped into a planographic printing press, where it gave more than 125,000 prints of excellent quality.

What is claimed is:

1. A compound having repeating units of the formula I

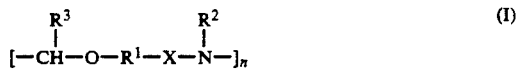

in which
R$^1$ is an alkylene, cycloalkylene, alkenylene, alkynylene, or arylenebisalkyl group, in which one or more aliphatic CH$_2$ groups may be replaced by oxygen or sulfur atoms,
R$^2$ is an alkyl, alkenyl, alkynyl, cycloalkyl, alkoxyalkyl, aryl, aralkyl or aryloxyalkyl radical,
R$^3$ is an alkyl or aryl radical,
X is —CO—, —O—CO— or —NH—CO—, and n is an integer greater than 1.

2. A compound as claimed in claim 1, wherein $R^1$ is an alkylene, alkenylene or alkynylene group each having 2 to 18 carbon atoms, in which 1 to 3 $CH_2$ groups are optionally replaced by oxygen or sulfur atoms, a cycloalkylene group having 4 to 18 carbon atoms, an aralkylene group having 7 to 18 carbon atoms or an arylenebisalkyl group having 8 to 18 carbon atoms.

3. A compound as claimed in claim 1, wherein $R^2$ is an alkyl radical having 1 to 12 carbon atoms, an alkenyl or alkynyl radical, each having 2 to 12 carbon atoms, an alkoxyalkyl radical having 3 to 12 carbon atoms, a cycloalkyl radical having 4 to 12 carbon atoms, an aryl radical having 6 to 12 carbon atoms, an aralkyl radical having 7 to 12 carbon atoms, or an aryloxyalkyl radical having 8 to 12 carbon atoms.

4. A compound as claimed in claim 1, wherein n is an integer from 3 to 50.

5. A compound as claimed in claim 1, wherein $R^3$ is an alkyl radical having to 6 carbon atoms, or a mononuclear or polynuclear aryl radical having 6 to 12 carbon atoms which may be substituted or unsubstituted.

6. A compound as claimed in claim 1, wherein $R^1$ is an unbranched or branched alkylene group having 2 to 4 carbon atoms, $R^2$ is an alkyl, alkenyl, alkynyl or cycloalkyl radical, each having up to six carbon atoms, and $R^3$ is an alkyl radical having 1 to 6 carbon atoms or an unsubstituted or substituted six-membered aryl radical.

7. A radiation-sensitive mixture which comprises
(a) at least one binder which is insoluble in water and soluble or at least swellable in aqueous alkaline solutions,
(b) at least one compound which generates a strong acid under the action of actinic radiation and
(c) a compound which has at least one acid-cleavable C—O—C bond and whose acid cleavage products are more readily soluble in aqueous alkaline solutions than the compound itself,
wherein the acid-cleavable compound (c) comprises at least one compound as claimed in claim 1.

8. A radiation-sensitive mixture as claimed in claim 7, wherein (b) comprises a compound sensitive to light of a wavelength from 150 to 550 nm.

9. A radiation-sensitive mixture as claimed in claim 7, which contains the compound (c) in a concentration from 1 to 60% by weight, based on the total weight of solids in the mixture.

10. A radiation-sensitive mixture as claimed in claim 7, wherein (a) has an extinction of less than 0.5 $\mu m^{-1}$ in the wavelength region of the sensitivity of (b).

11. A radiation-sensitive mixture as claimed in claim 10, wherein (a) comprises a polymer having at least one phenolic hydroxy group.

12. A radiation-sensitive mixture as claimed in claim 11 wherein (a) comprises a mixture of two or more polymers, each having at least one phenolic hydroxy group.

13. A radiation-sensitive mixture as claimed in claim 7, which contains (a) in a concentration from 30 to 95% by weight of the total solids in the mixture.

14. A radiation-sensitive mixture as claimed in claim 7, which contains (b) in a concentration from 0.2 to 25% by weight, based on the total weight of solids in the mixture.

15. A radiation-sensitive mixture as claimed in claim 7, wherein (b) comprises a compound which generates a sulfonic acid on photolysis.

16. A radiation-sensitive recording material comprising a support and a radiation-sensitive layer, wherein the layer comprises a radiation-sensitive mixture as claimed claim 7.

17. A method of producing a recording material as claimed in claim 16 which comprises applying said radiation-sensitive layer to said support.

18. A method as claimed in claim 17, comprising dissolving said mixture in a solvent, and applying the resultant solution to said support, and optionally, removing said solvent.

19. A method of preparing an image pattern comprising irradiating the radiation-sensitive layer of claim 16 imagewise, optionally heating the irradiated layer, treating the layer with a developer which removes the irradiated areas of the layer, and optionally post-hardening the developed layer structures.

20. A method as claimed in claim 17, which comprises first applying said radiation-sensitive layer to a temporary support, and then applying said support to said radiation-sensitive layer, and then optionally removing said temporary support.

* * * * *

UNITED STATES PATENT AND TRADEMARK OFFICE
CERTIFICATE OF CORRECTION

PATENT NO. : 5,286,602
DATED : February 15, 1994
INVENTOR(S) : PAWLOWSHI et al.

It is certified that error appears in the above-indentified patent and that said Letters Patent is hereby corrected as shown below:

Claim 16, Column 32, Line 27, "claimed claim 7" should read --claimed in claim 7--.

Signed and Sealed this

Twentieth Day of September, 1994

Attest:

BRUCE LEHMAN

Attesting Officer     Commissioner of Patents and Trademarks